United States Patent
Chung

(10) Patent No.: US 8,169,605 B2
(45) Date of Patent: May 1, 2012

(54) APPARATUS AND METHOD FOR INSPECTING LIQUID CRYSTAL DISPLAY

(75) Inventor: Han Rok Chung, Daegu (KR)

(73) Assignee: LG Display Co., Ltd., Seoul (KR)

( * ) Notice: Subject to any disclaimer, the term of this patent is extended or adjusted under 35 U.S.C. 154(b) by 355 days.

(21) Appl. No.: 12/218,064

(22) Filed: Jul. 11, 2008

(65) Prior Publication Data

US 2009/0015825 A1    Jan. 15, 2009

(30) Foreign Application Priority Data

Jul. 11, 2007   (KR) ................. 10-2007-0069858

(51) Int. Cl.
    *G01N 21/00*    (2006.01)
(52) U.S. Cl. ................................... 356/237.2
(58) Field of Classification Search ..... 356/237.1–237.6
    See application file for complete search history.

(56) References Cited

U.S. PATENT DOCUMENTS

| | | | | |
|---|---|---|---|---|
| 5,621,521 | A * | 4/1997 | Takahashi ................. | 356/237.1 |
| 7,166,856 | B2 * | 1/2007 | Cho et al. ................. | 250/559.45 |
| 7,202,695 | B2 * | 4/2007 | Chung et al. .............. | 324/770 |
| 7,253,795 | B2 * | 8/2007 | Tsunekawa et al. ........ | 345/87 |
| 7,283,227 | B2 * | 10/2007 | Dureiko .................... | 356/239.1 |
| 7,567,344 | B2 * | 7/2009 | LeBlanc et al. ............ | 356/239.1 |
| 2004/0246476 | A1 * | 12/2004 | Bevis et al. ............... | 356/237.5 |
| 2007/0206183 | A1 * | 9/2007 | Lebens .................... | 356/237.2 |

FOREIGN PATENT DOCUMENTS

KR    1020070034928    3/2007

* cited by examiner

*Primary Examiner* — Tarifur R. Chowdhury
*Assistant Examiner* — Isiaka O Akanbi
(74) *Attorney, Agent, or Firm* — McKenna Long & Aldridge, LLP

(57) ABSTRACT

A method of inspecting a liquid crystal display panel includes providing a liquid crystal display panel to be inspected, turning on a backlight unit that is disposed under the liquid crystal display panel to emit light toward the liquid crystal panel, driving the liquid crystal display panel by applying test signals to the liquid crystal display panel on a predetermined period, detecting defects by taking an image of the liquid crystal display panel on a period shorter than the driving period of the liquid crystal display panel, and detecting defects created in the liquid crystal display panel, which blink in accordance with a period of the test signals of the liquid crystal display panel.

8 Claims, 5 Drawing Sheets

APPARATUS AND METHOD FOR INSPECTING LIQUID CRYSTAL DISPLAY

The present application claims priority under 35 U.S.C. 119 and 35 U.S.C. 365 to Korean Patent Application No. 10-2007-0069858, filed on Jul. 11, 2007, which is hereby incorporated by reference for all purposes as if fully set forth herein.

BACKGROUND OF THE INVENTION

1. Field of the Invention

The present invention relates to an apparatus and method for inspecting a liquid crystal display.

2. Discussion of the Related Art

As the information-oriented society has arrived, a requirement for flat panel displays that are light and thin and have lower power consumption is on the rise.

Among the flat panel displays, liquid crystal displays have been widely used for laptop computers and desktop computers.

Generally, a liquid crystal display includes two substrates facing each other, electric field generating electrodes formed on inner surfaces of the substrates, and a liquid crystal material injected in a space defined between the substrates. When a voltage is applied to the electrodes, liquid crystal molecules are twisted by an electric field to vary transmittance of the light, by which an image is displayed.

In the related art, many inspection processes are performed in the course of manufacturing the liquid crystal display. Particularly, after an array substrate is made, an array test process is performed to check for a pixel defect and a line cut, and the like. After the array substrate is attached to a color filter substrate, a lightening test for the liquid crystal panel is performed in a cell process.

In the cell process, an auto-probe device is used to allow a proof pin to contact the liquid crystal panel, after which a tester checks for the defect of the liquid crystal panel through a test using an optical device and his/her eyes in a state where the liquid crystal panel is driven.

That is, after the test signal is applied to the liquid crystal panel in the auto-probe device, a light source of a backlight is variously turned on to inspect a point defect and a line defect of the liquid crystal panel.

However, the test method of the related art has the following limitations.

First, as the liquid crystal display is enlarged above 40 inches, the test using the tester's eyes has a limitation.

Second, since the point and line defects of the liquid crystal panel are performed by the tester, after selecting defect candidates in advance, determining pass or fail by precisely inspecting the liquid crystal panel, it takes long time to perform the test.

Third, for the point defect, it is difficult to discriminate between a foreign substance on an outer surface of the liquid crystal panel or a polarizing panel and a foreign substance on an inner surface of the liquid crystal panel.

Particularly, the point defect caused by the foreign substance on the inner surface of the liquid crystal panel is a real defect that is directly related to the defect of the liquid crystal panel. Therefore, an accurate inspection for the point defect is required. However, the inspection method of the related art cannot perform the accurate inspection.

SUMMARY OF THE INVENTION

Accordingly, the present invention is directed to an apparatus and method for inspecting liquid crystal display that substantially obviate one or more of the problems due to limitations and disadvantages of the related art.

An advantage of the present invention is to provide an apparatus and method of inspecting a liquid crystal display, which can accurately inspect a foreign substance generated inside a liquid crystal panel by adjusting an image capturing speed of a camera and a driving interval of the liquid crystal panel.

Additional features and advantages will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purposes of the present invention, a method of inspecting a liquid crystal display includes providing a liquid crystal panel to be inspected, turning on a backlight unit that is disposed under the liquid crystal panel to emit light toward the liquid crystal panel, driving the liquid crystal panel by applying test signals to the liquid crystal panel on a predetermined panel, detecting defects by taking an image of the liquid crystal panel on a period shorter than the driving period of the liquid crystal panel, and detecting defects created in the liquid crystal panel, which blink in accordance with a period of the test signal of the liquid crystal panel.

In another aspect of the present invention, an apparatus for inspecting a liquid crystal display includes a camera disposed above a liquid crystal panel, a backlight unit disposed under the liquid crystal panel, a driving unit for driving the camera, liquid crystal panel, and backlight unit, and an inspecting unit for storing defect information taken by the camera.

It is to be understood that both the foregoing general description and the following detailed description are exemplary and explanatory, and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention.

In the drawings.

DETAILED DESCRIPTION OF THE ILLUSTRATED EMBODIMENTS

Reference will now be made in detail to embodiments of the present invention, examples of which are illustrated in the accompanying drawings.

Figure 1:
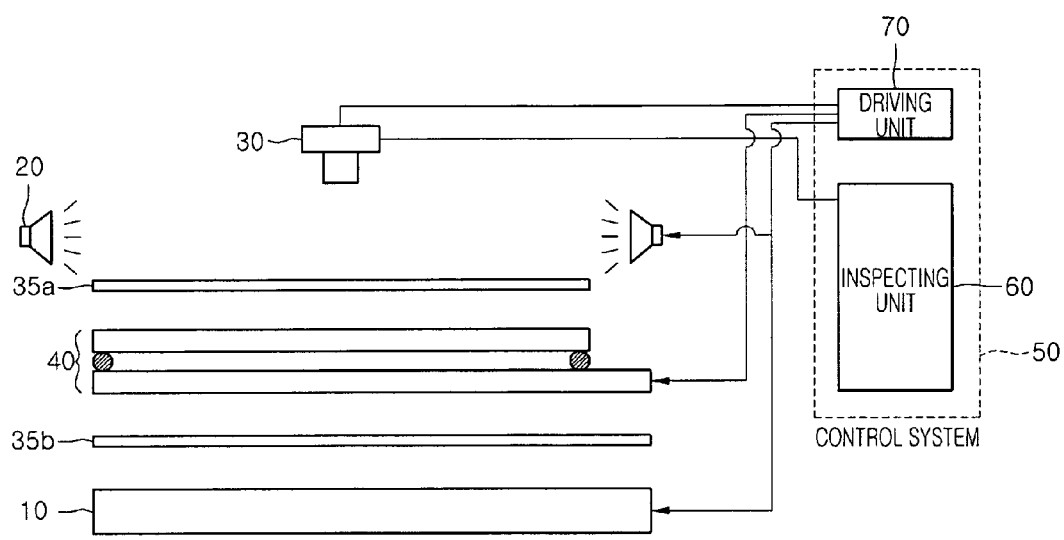
FIG. 1 is a schematic view of an apparatus for inspecting a liquid crystal display according to an embodiment.

FIG. 1 is a schematic view of an apparatus for inspecting a liquid crystal display according to an embodiment.

As shown in FIG. 1, a liquid crystal display includes a liquid crystal display panel 40, upper and lower polarizing plates 35a and 35b disposed on top and bottom surfaces of the liquid crystal display panel 40, and a backlight unit 10 disposed under the lower polarizing plate 35b. A camera 30 for inspecting foreign substances on the upper and lower polarizing plates 35a and 35b and a point or line defect of the liquid crystal display 40 is disposed above the upper polarizing plate 35a. Side light generating units 20 are disposed at left and right sides of the liquid crystal panel 40. A control system 50 is provided to control the defect inspection.

The control system 50 includes a driving unit 70 for selectively or wholly driving the camera 30, side light generation unit 20, liquid crystal display panel 40, and backlight unit 10 and an inspecting unit 60 for storing and reading defect information taken by the camera 30.

Here, the liquid crystal display panel 40 includes an array substrate on which a plurality of gate lines extending in a direction and spaced apart from each other, and a plurality of data lines extending a direction perpendicular to the gate lines, a plurality of thin film transistors formed at matrix pixel regions defined by the gate and data lines, and a plurality of pixel electrodes, a color filter substrate having a black matrix and a color filter layer, and a liquid crystal layer disposed between the array and color filter substrates that are attached to each other.

The camera 30 is disposed above the liquid crystal display panel 40 and is capable of moving upward, downward, leftward, and rightward. That is, the camera 30 takes an image while scanning in a horizontal direction and moving in a vertical direction.

The following will describe an apparatus and method for inspecting the liquid crystal display panel according to an embodiment.

First, point and line defects for an entire region of the liquid crystal display panel 40 are inspected by the turning on/off of the backlight unit 10 and operation of the liquid crystal panel 40 and camera 30. At this point, the backlight unit 10 is turned on and off by the driving unit 70 of the control system 50. The liquid crystal display panel 40 is also driven in accordance with test signals red, green, and blue signals applied from the driving unit 70. Therefore, the light generated by the backlight unit 10 is polarized while passing through the lower polarizing plate 35b and subsequently passes through the liquid crystal display panel 40. The light travels to the upper polarizing plate 35a to realize a desired test image.

At this point, the camera 30 takes a front image of the liquid crystal display panel 40 or takes an entire region of the liquid crystal display panel 40 while scanning in a predetermined direction to detect the locations and number of defects. When the defects are detected, the defect information is stored in an inspection unit 60 of the control system 50.

Therefore, point defects of the defect information stored in the inspection unit 60 include all defects formed inside and outside of the liquid crystal display panel 40 and on the upper and lower polarizing plates 35a and 35b.

After the above, the driving unit 70 of the control system 50 turns on and off the side light generating unit 20 and inspects for foreign substances generated on the surface of the liquid crystal display panel 40 or the surface of the upper polarizing plate 35a.

The defects detected by the driving of the side light generating unit 20 include defects generated on the surface of the liquid crystal display panel 40 or the surface of the lower polarizing plate 35b.

As described above, when the defect inspection by the side light generating unit 20 is completed, a real defect inspection is performed by the liquid crystal display panel 40 and the adjustment of an image take speed (image take period) of the camera 30. The real defects include foreign substance defects generated at the pixel regions on the inner surface of the surfaces facing each other or between the liquid crystal layer and the substrates.

In the real defect inspection method, the backlight unit 10 is periodically turned on and off and the liquid crystal display panel 40 is driven on a period shorter than the turning-on period of the backlight unit 10 (e.g., on a period half the turning-on period of the backlight unit 10. In addition, the image take speed of the camera 30 is set to be shorter than the driving period of the liquid crystal display panel 40 (e.g., ¼ of the backlight turning-on period). At this point, the side light generating unit 20 may be driven or not Thus, since the turning-on period of the backlight unit 10 is longest, it is recognized that the backlight unit 10 is always in the on-state on the camera's part and the liquid crystal display panel's part. Since the liquid crystal display panel 40 is turned on/off by at least one time during the on-state of the backlight unit 10, defects existing inside the liquid crystal display panel 40 are detected in a blinking state.

That is, defects are detected in a white or black color in accordance with the twisting or the non-twisting of liquid crystal molecules in the liquid crystal panel 40.

Since the camera 30 takes successively the images at a speed faster than the driving period of the liquid crystal display panel 40, it can detect bright points and dark points generated by the defects inside the liquid crystal display panel 40.

That is, the image take speed of the camera 30 is much faster than the driving speed (on/off of liquid crystal molecules) of the liquid crystal display panel 40, the camera 30 can detect all of the states that are varied depending on the operation of the liquid crystal display panel 40.

Therefore, in the embodiment, all of the foreign substance defects are inspected by the operation of the backlight 10 and the camera 30 (the number of the defects is "m") and the foreign substance defects on the polarizing plate and an outer surface of the liquid crystal display panel are inspected by the operation of the side light generating unit 20 (the number of defects is "n"). The number of real defects generated inside the liquid crystal display panel 40 can be accurately detected using a different between the defect numbers (m−n).

In addition, in the embodiment, by adjusting the image take speed of the camera 30, the driving time of the liquid crystal display panel 40, and the turning-on time of backlight unit 10, the defects generated inside the liquid crystal display panel 40 periodically blink and thus the real defects can be accurately inspected.

Figure 2A:
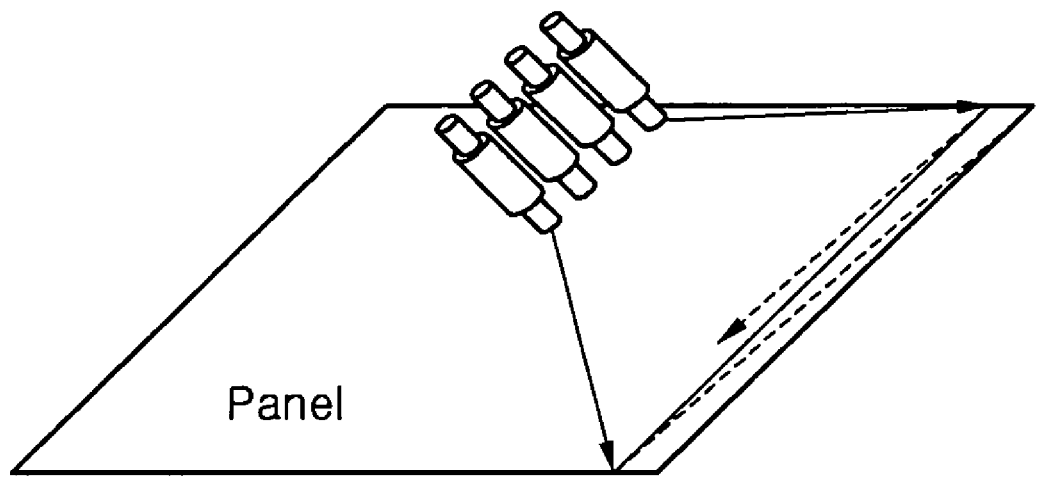
FIGS. 2A and 2B are views illustrating a method of inspecting a liquid crystal display using a camera of an inspection apparatus according to an embodiment.
Figure 2B:
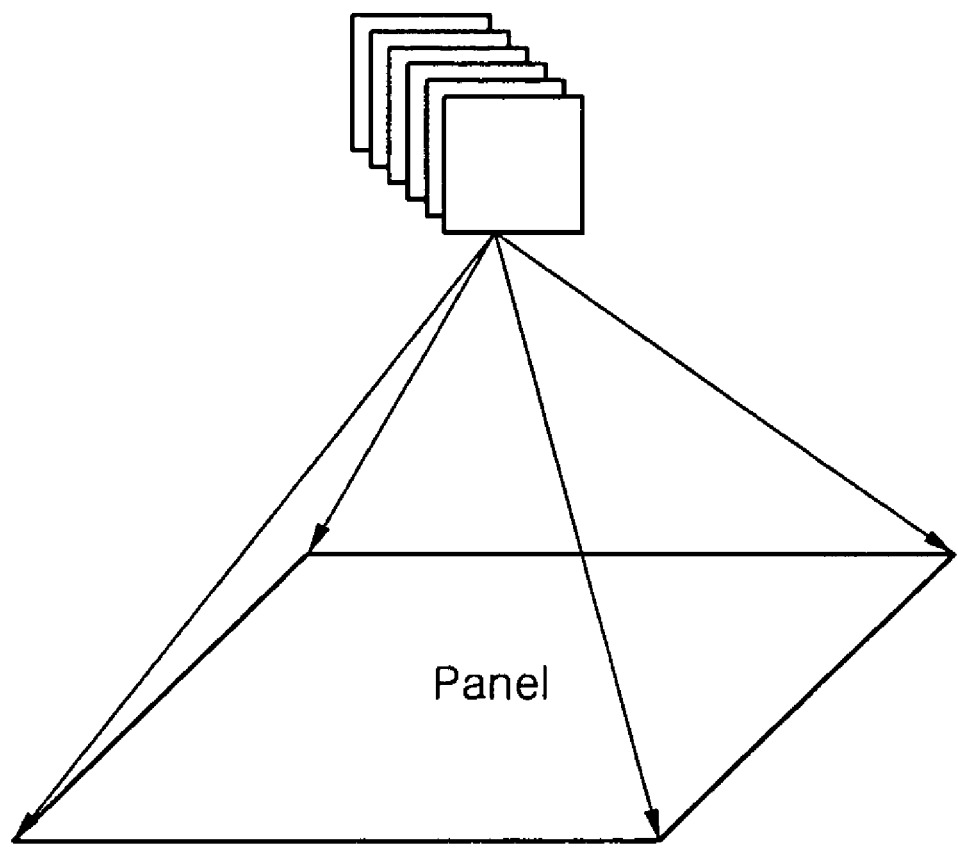

FIGS. 2A and 2B are views illustrating a method of inspecting a liquid crystal panel display using a camera of an inspection apparatus according to an embodiment. FIG. 2A illustrates a method for inspecting an entire region of liquid crystal display panel by scanning the liquid crystal panel in a substantially horizontal direction at an upper portion and moving the camera in a substantially perpendicular direction. FIG. 2B illustrates a method for inspecting the entire region of the liquid crystal display panel by disposing the camera above the liquid crystal display panel such that the entire region of the liquid crystal display panel can be included in an image taking range of the camera.

A light intensity adjustor may be attached on the camera of the inspection apparatus. By the light intensity adjustor, a standard by which the defect is determined can be adjusted in accordance with a luminance of scattered light.

Figure 3:
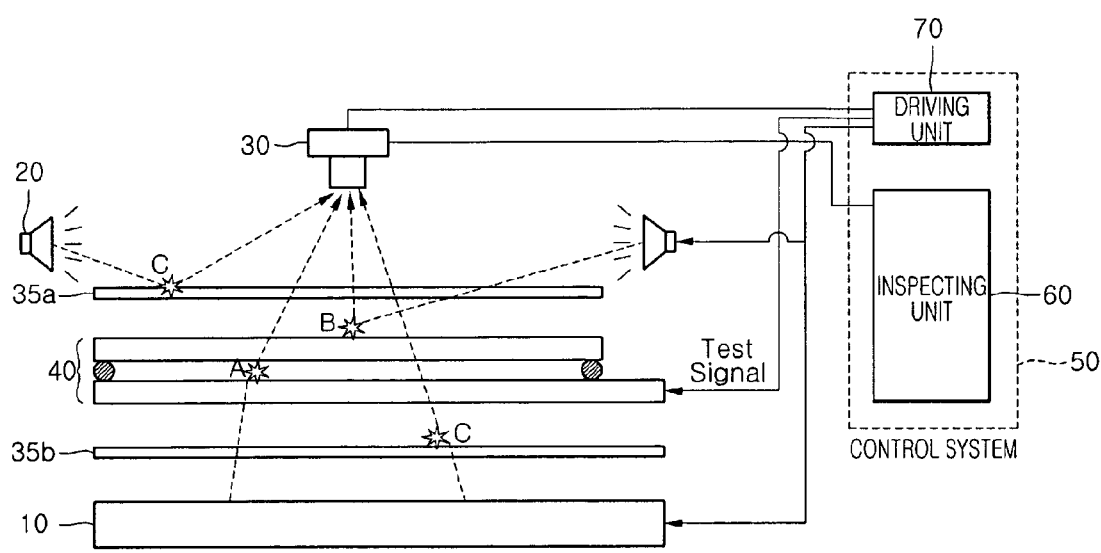
FIG. 3 is a view illustrating a liquid crystal display inspection process according to an embodiment.

FIG. 3 is a view illustrating a liquid crystal display panel inspection process according to an embodiment.

Since the liquid crystal display panel inspecting apparatus is as that of FIG. 1, like reference numbers will be used to refer to like parts.

As shown in FIG. 3, the backlight unit 10 is turned on and the red, green, and blue signals (test signals) for inspecting the liquid crystal display panel 40 are applied. Subsequently, defects are detected using the method described in FIGS. 2A and 2B.

Therefore, the camera 30 detects defects A inside the liquid crystal panel 40, defects B outside the liquid crystal panel 40, and defects C on the upper and lower polarizing plates 35a and 35b. Information on the location and number of the detected defects is stored in the inspection unit 60 of the control system 50.

Next, by driving the side light generating unit 20, the outside defect B of the liquid crystal display panel 40 and the defects C on the upper and lower polarizing plates 35a and 35b are detected. The information on the detected defects is stored in the inspection unit 60 of the control system 50.

After the above, real defects A inside the liquid crystal display panel 40 are extracted by subtracting the defects detected by the side light generating unit 20 from all of the defects.

Here, the real defects A are defects generated inside the liquid crystal display panel 40, which cannot be removed through a simple cleaning process. Therefore, it is important to identify the accurate locations of the real defects A.

Figure 4A:
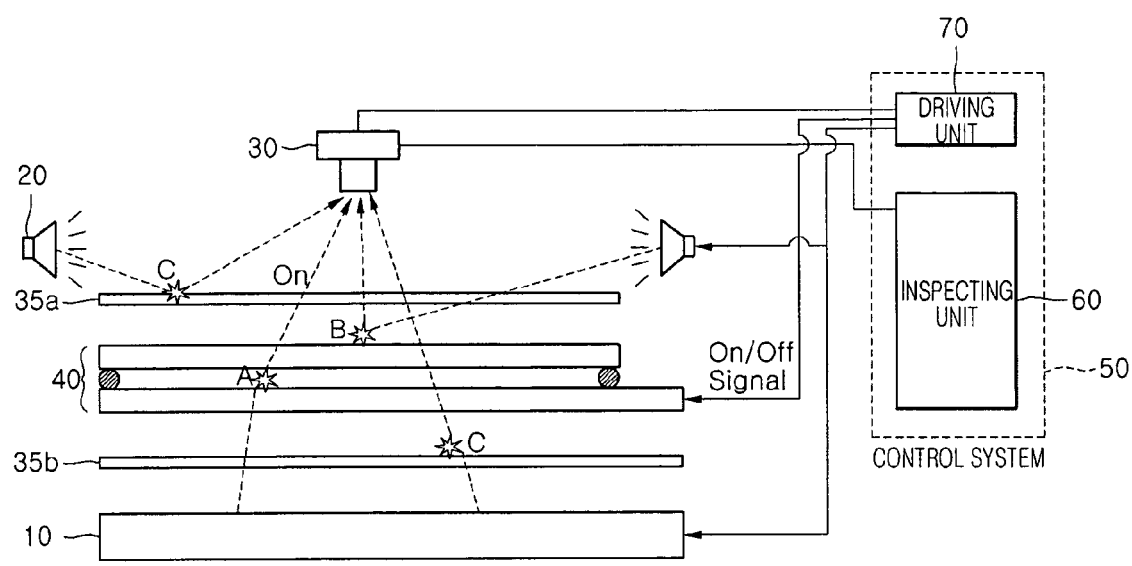
FIGS. 4A and 4B are views illustrating an inspection process for a real defect generated inside a liquid crystal panel according to an embodiment.
Figure 4B:
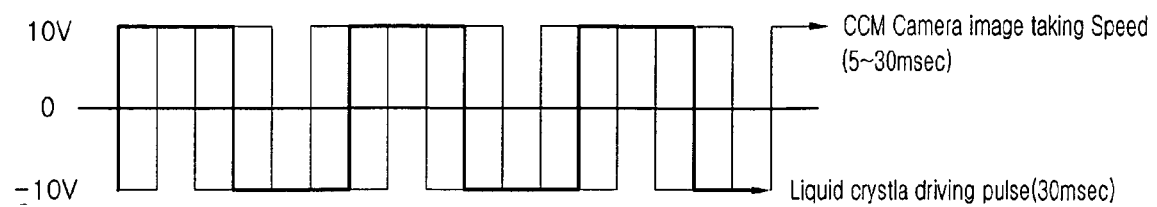

FIGS. 4A and 4B are views illustrating an inspection process for a real defect generated inside a liquid crystal display panel according to an embodiment.

As shown in FIGS. 4A and 4B, by making the turning-on period of the backlight unit 10 longer than the driving period of the liquid crystal display panel 40 and the image taking period of the camera 30, the backlight unit 10 maintains the turning-on state when the liquid crystal display panel 40 is driven and the camera 40 takes an image.

Next, by making the image taking speed (image taking period) of the camera shorter than the driving period of the liquid crystal display panel 40, the defects A generated inside the liquid crystal display panel 40 are detected. For example, when the driving pulse period of the liquid crystal display panel 40 is 30 msec, the image taking speed of the camera 30 is set to have 5-30 msec shorter than 30 msec.

In addition, test signals applied to the liquid crystal display panel 40 are switching signals that turn on/off in a vertical direction (TN mode) or in a horizontal direction (IPS mode).

When the driving period of the backlight unit 10, the driving period of the liquid crystal display panel 40, and the image taking period of the camera 30 as described above, the backlight unit 10 maintains the turning-on state when the liquid crystal display panel 40 and the camera 30 operate and thus the defects A, B, and C are detected by the camera 30 as they are in a white state. At this point, the side light generating unit 20 may be in an on-state or an off-state.

Since the image taking speed of the camera 30 is much faster than the driving periods of the backlight unit 10 and liquid crystal display panel 40, all of the defects A, B, and C can be primarily detected. Particularly, since the on/off signals are applied to the liquid crystal display panel 40, the defects B existing in the liquid crystal display panel 40 are detected as they blink.

As shown in the drawings, when the off signal is applied to the liquid crystal display panel 40, the liquid crystal molecules in the liquid crystal display panel 40 intercept light from the backlight unit 10 and thus the light is detected by the camera 30 as they are in a black state.

Therefore, by simply adjusting the turning-on period of the backlight unit 10, the driving period of the liquid crystal display panel 40, and the image taking period of the camera 30, real defects A existing in the liquid crystal panel 40 and foreign substance defects existing on the upper and lower polarizing plates 35a and 35b and on the outside of the liquid crystal display panel 40 can be detected.

As described above, by adjusting the driving period of the liquid crystal display panel 40 and the image taking period of the camera 30, the real defects generated in the liquid crystal display panel can be accurately detected.

It will be apparent to those skilled in the art that various modification and variations can be made in the present invention. Thus, it is intended that the present invention covers the modifications and variations of this invention provided they come within the scope of the appended claims and their equivalents.

What is claimed is:

1. A method of inspecting a liquid crystal display panel, comprising:
    providing a liquid crystal display panel to be inspected;
    turning on a backlight unit that is disposed under the liquid crystal display panel to emit light toward the liquid crystal display panel;
    driving the liquid crystal display panel by applying test signals to the liquid crystal display panel at a predetermined period;
    detecting defects by taking an image of the liquid crystal display panel on a period shorter than the driving period of the liquid crystal display panel; and
    detecting defects created in the liquid crystal panel, which blink in accordance with a period of the test signals of the liquid crystal display panel,
    wherein the backlight unit is periodically turned on and off and the liquid crystal display panel is driven on a period shorter than the turning-on period of the backlight unit,
    wherein when the liquid crystal display panel is turned on/off by at least one time during the on-state of the backlight unit, defects existing inside the liquid crystal display panel are detected in a blinking state,
    wherein a driving period of the liquid crystal display panel is set on a period half the turning-on period of the backlight unit, the image take speed of the camera is set on ¼ of the backlight turning-on period.

2. The method according to claim 1, wherein the detecting of the defects by taking the image includes defecting all defects generated at an inside and an outside of the liquid crystal display panel and on the upper and lower polarizing plates.

3. The method according to claim 2, wherein the defects at the inside and outside of the liquid crystal display panel and on the upper and lower polarizing plates are detected in a white state.

4. The method according to claim 1, wherein the driving period of the liquid crystal display panel is 30 msec and repeats an on/off switching in a vertical or horizontal direction.

5. The method according to claim 1, further comprising turning on side light generating units disposed at both sides of the liquid crystal display panel when the backlight unit is turned on.

6. An apparatus for inspecting a liquid crystal display panel, comprising:
    a camera disposed above a liquid crystal display panel;
    a backlight unit disposed under the liquid crystal display panel;

a driving unit for driving the camera, liquid crystal display panel, and backlight unit;

a side light generating units disposed at both sides of the liquid crystal display panel; and an inspecting unit for storing defect information taken by the camera, wherein when the defect inspection by the side light generating units is completed a real defect inspection is performed by the liquid crystal display panel and the adjustment of an image take speed of the camera, wherein the backlight unit is periodically turned on and off and the liquid crystal display panel is driven on a period shorter than the turning-on period of the backlight unit in the real inspection, wherein the image take speed of the camera is set to be shorter than the driving period of the liquid crystal display panel in the real inspection, wherein a driving period of the liquid crystal display panel is set on a period half the turning-on period of the backlight unit, the image take speed of the camera is set on ¼ of the backlight turning-on period.

7. The apparatus according to claim 6, wherein the defect information stored in the inspecting unit includes location and number information of real defects generated inside the liquid crystal display panel and location and number information of defect generated outside the liquid crystal display panel.

8. The apparatus according to claim 6, wherein the driving unit drives the backlight unit, the liquid crystal display panel, and the camera by making a turning-on period of the backlight unit, a driving period of the liquid crystal display panel, and an image taking period of the camera different from each other.

* * * * *